(12) United States Patent
Glynne Jones et al.

(10) Patent No.: US 8,017,557 B2
(45) Date of Patent: Sep. 13, 2011

(54) BENZODIOXOLE DERIVATIVES AS MODULATORS OF PROTEOLYTIC ACTIVITY IN PLANTS

(75) Inventors: George Denys Glynne Jones, Wendover (GB); Valerio Borzatta, Bologna (IT)

(73) Assignee: Endura S.p.A., Bologna (IT)

( * ) Notice: Subject to any disclaimer, the term of this patent is extended or adjusted under 35 U.S.C. 154(b) by 0 days.

(21) Appl. No.: 10/504,367

(22) PCT Filed: Feb. 13, 2003

(86) PCT No.: PCT/EP03/01425
§ 371 (c)(1),
(2), (4) Date: Aug. 12, 2004

(87) PCT Pub. No.: WO03/067985
PCT Pub. Date: Aug. 21, 2003

(65) Prior Publication Data
US 2005/0085390 A1    Apr. 21, 2005

(30) Foreign Application Priority Data

Feb. 14, 2002    (IT) .............................. MI2002A0287

(51) Int. Cl.
*A01N 43/08* (2006.01)
(52) U.S. Cl. ...................................... 504/298
(58) Field of Classification Search .................. 504/296
See application file for complete search history.

(56) References Cited

U.S. PATENT DOCUMENTS

| | | | | |
|---|---|---|---|---|
| 3,899,586 A | * | 8/1975 | Okuno et al. | 514/417 |
| 4,056,610 A | * | 11/1977 | Barber et al. | 424/419 |
| 5,326,560 A | * | 7/1994 | Henderson | 424/93.461 |
| 5,856,526 A | * | 1/1999 | Sankaram et al. | 549/348 |

FOREIGN PATENT DOCUMENTS

| | | |
|---|---|---|
| EP | 0 502 730 B1 | 9/1992 |
| EP | 0 339 009 B1 | 8/1993 |
| GB | 2127691 * | 4/1984 |

OTHER PUBLICATIONS

[No Author Listed] Enzyme Kinetics. in Quantitative Problems in Biochemistry. Edwin A. Dawes, editor. The Williams and Wilkins Company, 1972; p. 210-8.

Alzogaray et al., Third instar nymphs of *Rhodnius prolixus* exposed to alpha-cyanopyrethroids: from hyperactivity to death. Arch Insect Biochem Physiol. Mar. 2001;46(3):119-26. Abstract Only.
Bohlmann et al., The role of thionins in plant protection. Crit Rev Plant Sci. 1994; 13(1): 1-16.
Erlanger et al., The preparation and properties of two new chromogenic substrates of trypsin. Arch Biochem Biophys. Nov. 1961;95:271-8.
Funkhouser et al., Endopeptidase activity in cotton cotyledons during development. Z Pflanznphsyiol Bd. 1980; 100: S319-24.
Gunning et al., Chapter 13: Inhibition of resistance-related esterases by piperonyl butoxide in *Helicoverpa armigera* (Lepidoptera: Noctuidae) and *Aphis gossypii* (Hemiptera: Aphididae). in Piperonyl Butoxide: The Insecticide Synergist. Denys G. Jones, editor. Academic Press, 1998; p. 215.
Harsulkar et al., Successive use of non-host plant proteinase inhibitors required for effective inhibition of *Helicoverpa armigera* gut proteinases and larval growth. Plant Physiol. Oct. 1999;121(2):497-506.
Heinrikson et al., Chapter 64: Acidic cysteine protease inhibitors from pineapple stem. in Naturally Occurring Protease Inhibitors. p. 740-51.
Ihle et al., The developmental biochemistry of cottonseed embryogenesis and germination. I. Purification and properties of a carboxypeptidase from germinating cotyledons. J Biol Chem. Aug. 25, 1972;247(16):5034-40.
Kotze, Cytochrome P450 monooxygenase activity in *Haemonchus contortus* (Nematoda). Int J Parasitol. Jan. 1997;27(1):33-40. Abstract Only.
Leah et al., Biochemical and molecular characterization of three barley seed proteins with antifungal properties. J Biol Chem. Jan. 25, 1991;266(3):1564-73.
MacIntosh et al., Potentiation of *Bacillus thuringiensis* insecticidal activity by serine protease inhibitors. J Agric Food Chem. 1990; 38: 1145-52.
Santarius et al., Radial diffusion as a sensitive method for screening endopeptidase activity in plant extracts. Anal Biochem. Jan. 1977;77(1):1-9.
Walde et al., Structure and activity of trypsin in reverse micelles. Eur J Biochem. Apr. 15, 1988;173(2):401-9.
Ugolini et al., "Benzodioxole Derivatives as Negative Effectors of Plant Proteases," *J. Agric. Food Chem.*, vol. 53, pp. 7494-7501, 2005.

* cited by examiner

*Primary Examiner* — Alton Pryor
(74) *Attorney, Agent, or Firm* — Wolf, Greenfield & Sacks, P.C.

(57) ABSTRACT

The present invention has as subject, the use of benzodioxole derivatives as modulators of the activity or of the content of protein hydrolases in plants. Such a new use allows the increase of the natural or induced defences of the plant.

21 Claims, 8 Drawing Sheets

difference%
treated minus control

BENZODIOXOLE DERIVATIVES AS MODULATORS OF PROTEOLYTIC ACTIVITY IN PLANTS

RELATED APPLICATIONS

This application is a national stage filing under 35 U.S.C. §371 of PCT International application PCT/EP2003/001425, filed Feb. 13, 2003, which was published under PCT Article 21(2) in English.

FIELD OF THE INVENTION

The invention relates to the use of benzodioxole derivatives to modify enzyme activity in plants.

STATE OF THE ART

Piperonyl butoxide is a benzodioxole polyoxyethylene known for some time as a synergist of insecticides such as for example of pyrethrins, pyrethroids and carbamate types insecticides.

Its relatively low toxicity with regard to humans and animals and its appreciable effects on a large spectrum of insecticides has allowed its use to spread rapidly in agriculture.

The mechanisms at the heart of this synergistic effect have not yet been clarified, even if from time to time direct or indirect regulation effects on some specific enzymes involved in the inactivation or in the catabolism of the insecticide molecules with which it synergises have been proposed, such as for example non specific esterases present in insect homogenates (Piperonyl Butoxide "The insecticide Synergist", 1998, Academic Press, p. 215), more recently on microsomal oxidases (Alzogaray R. A. Arch. Insect Biochem. Physiol., 2001, 46:119-126), or on cytochrome P450 mono oxygenases (Kotze et al. Int. J. Parasitol, 1997, 27:33-40). However, as yet, an effect of PBO on enzymes of plant origin has not been described, let alone in particular on the proteolytic or peptidase class of enzymes.

The significance of the proteases and their physiological inhibitors as key enzymes in the regulation of cellular processes both in the animal and plant kingdoms is known and widely recognised.

In plants, for example, the balance between proteolytic enzymes and natural inhibitors is at the heart of the precise temporal regulations of the germination process of dormant seeds.

It is also known that over the course of evolution, the production of natural inhibitors of proteolytic enzymes has been selected in plants, among others, as a protection mechanism against parasites. The usefulness of interventions based on this type of approach is confirmed for example in Harsulkar A. M. et al. Plant Physiol., 1999, 121:497-506. An approach based on the use of protease inhibitors expressed transgenically, is described in EP 502730 and in EP 339009: in the first the expression of the inhibitor is sufficient to determine a protective effect against nematodes, in the second, the transgenic expression of a natural protease inhibitor potentiates the insecticide effect of the product of the first gene encoding the Bt toxin (*Bacillus thuringiensis* toxin). The same approach is described by S. MacIntosh et al. in J. Agric. Food Chem. 1990, 38:1145-1152.

It is therefore evident that the availability of a product endowed with regulatory activity of the activity of proteolytic enzymes of plant origin is of great industrial interest for a wide spectrum of applications.

SUMMARY OF THE INVENTION

The object of the present invention is the use of benzodioxole derivatives of formula I, amongst which the preferred is piperonyl butoxide (PBO) as modulators of the activity or of the content of proteolytic enzymes in plants. Proteolytic enzymes able to hydrolyse peptide bonds, are preferably selected from the group consisting of: carboxypeptidases, aminopeptidases, dipeptidases, endopeptidases.

Treatment with benzodioxole derivatives is carried out on plants, preferably transgenic for a protein with insecticidic function, preferably belonging to the category of the *Bacillus thuringiensis* toxins (Bt-toxin), belonging to the Cry group. Preferably such transgenic plants are cotton, maize, tomato, potato and soya, or even more preferably, cotton.

According to a further aspect the invention extends to the use of compositions containing the benzodioxole derivatives as the active ingredients in combination with suitable emulsifiers and optionally with photoprotective compounds selected from the group consisting of: benzotriazoles, benzophenones and sterically hindered amines, as modulators of the activity or of the content of proteolytic enzymes in plants.

According to a further aspect the invention extends to a process for regulating the proteolytic activity in plants, preferably transgenic, even more preferably cotton, maize, soya, tomato, potato comprising essentially the treatment of such plants with benzodioxole derivatives and with the compositions containing such compounds, in a way such that the final concentration of PBO is comprised of between 50 and 500 grams/hectare and is performed at the end of the vegetative cycle.

BRIEF DESCRIPTION OF THE FIGURES

Abscissa: PBO concentration (M); ordinate: I/V (Δ Abs/min). Reverse micelles assay ISO-AOT 50 mM (AOT: double aerosol (2-ethylhexylsodiumsulfosuccinate in isooctane (ISO)); $W_o$ ($H_2O$/AOT)=23

From the Dixon diagram obtained at two different substrate concentrations (CBZ: L lysine-p-nitrophenyl ester), used at $1.5 \times 10^{-4}$ M (full circle -●-) and $6 \times 10^{-5}$ M (empty circle -○-) respectively, it is possible to calculate the inhibition constant ($K_I$) of PBO on the enzyme ficin, equal to $0.45 \times 10^{-3}$M. From the diagram it is also possible to evaluate the $IC_{50}$ equal to $0.8 \times 10^{-3}$M.

Abscissa: PBO concentration (M), ordinate: I/V (Δ Abs/min). Reverse micelles assay of ISO-AOT 50 mM (AOT: twin aerosol (2-ethylhexylsodiumsulfosuccinate in isooctane (ISO)); $W_o$ ($H_2O$/AOT)=25

From the Dixon-plot obtained at two different substrate concentrations (CBZ: L lysine-p-nitrophenyl ester), used at $1.5 \times 10^{-4}$ M (full circle -●-) and $6 \times 10^{-5}$ M (empty circle -○-)

respectively, it is possible to calculate the inhibition constant ($K_I$) of PBO on the enzyme bromelain, equal to $0.1 \times 10^{-3}$ M. In addition from the plot it is possible to evaluate the $IC_{50}$ equal to $0.4 \times 10^{-3}$ M.

Abscissa: PBO concentration (M), ordinate: I/V (Δ Abs/min). Reverse micelles assay of ISO-AOT 50 mM (AOT: twin aerosol (2-ethylhexylsodiumsulfosuccinate in isooctane (ISO)); $W_o$ ($H_2O$/AOT)=28

The extent of proteolytic activity in cotton sprouts was measured at 30', 60', 90' and 1.20° after suspension of the acetonic powder in aqueous buffer at pH 6.5 by determining the absorbance at 280 nm in a quartz cuvette, after protein precipitation with TCA and removal by centrifugation.

Each series of analysis was performed in duplicate. The comparison between the values of carboxypeptidase activity of treated and untreated samples was done using the average value of each series of analysis.

Treated samples: dark grey
Untreated samples: light grey

The extent of hydrolytic activity in cotton sprouts was measured at 15', 30', 60', 90' and 120' after solubilization of the acetonic powder in aqueous buffer at pH 7.7 by determining the absorbance at 280 nm in a quartz cuvette after protein precipitation with TCA and removal by centrifugation. Each series of analysis was performed in duplicate. The comparison between the values of carboxypeptidase activity in treated (dark grey) and untreated (light grey) samples was done using the average value of each series of analysis. Abscissa: time (min); ordinate: Abs 280 nm.

An immunoenzymatic assay was used to determine the Bt levels at different stages of plant development.
a) Measured Bt toxin values; ordinate: Bt expressed as ppm; abscissa: days of plant culture and where different, plant tissue. Black col.: Untreated cotton; grey col: PBO treated cotton. Standard deviation is also indicated.
b) % differences in Bt content during time in PBO treated vs untreated plants. Ordinate: % Bt content (ppm) in PBO treated minus untreated plants; abscissa: days of plant culture and where different, plant tissue (cotyledons or leaves).

FIG. 7. Comparison between endopeptidase activity of treated with PBO and untreated cotton plants at different growing stages by the Radial Diffusion Assay.

The radium of the clear zone produced by the plant extracts was compared to a standard curve obtained by a serial dilution of trypsin. A standard solution of trypsin was used to plot a standard curve for each sample plate, thus the endopeptidase activity was expressed as units of trypsin equivalents. For each extract, the amount of soluble proteins in mg was determined by the Biuret method and the enzymatic activity was then expressed as specific activity i.e. Units/mg soluble proteins. Abscissa: time (days); ordinate: trypsin units/mg soluble protein.

FIG. 8. Comparison between peptidase activity (U/mg of soluble protein) of PBO treated and untreated cotton plants by a photometric assay with DL-BAPA as a substrate.

The photometric assay was carried out following the DL-BAPA hydrolysis at 410 nm. One peptidase unit (U) was defined as the amount of the enzyme, which produces one unit of absorbance variation at 410 nm/minute at pH 8.2 and 30° C. For each extract, the amount of soluble proteins in mg was determined by the Biuret method and the enzymatic activity was then expressed as specific activity i.e. Units/mg soluble proteins.

Each analysis was performed in duplicate or in triplicate and the standard deviation for each point is also indicated. Abscissa: time (days); ordinate: trypsin units/mg soluble protein.

DETAILED DESCRIPTION OF THE INVENTION

The present invention relates to the use of benzodioxole derivatives comprised in the following general formula I:

(I)

wherein $R_1$, $R_2$ and $R_3$ being the same or different are selected from the group consisting of: hydrogen; alkyl $C_2$-$C_8$; $CH_2OR_4$ where $R_4$ is selected from the group consisting of: hydrogen, $-(CH_2CH_2O)_n-R_5$, in which n is an integer from 1 to 4 and $R_5$ is selected from the group consisting of: hydrogen, alkyl $C_1$-$C_8$, aryl non substituted or substituted by: alkyl $C_1$-$C_4$, halogen, cyano group (CN), $-SO_3H$ group, carboxyalkyl group $-COOR_6$, (where $R_6$ is hydrogen or alkyl $C_1$-$C_8$), a $-N(R_7)-R_8$ group, where $R_7$ and $R_8$ being the same or different are: hydrogen or alkyl $C_1$-$C_4$ or together with the atom of nitrogen to which they are bound, representing a piperidinyl, pyrrolidine, morpholine group;

$R_5$ is in addition selected from the group consisting of aralkyl $C_7$-$C_9$ non substituted or substituted on the aromatic ring by substituents selected from the group consisting of: alkyl $C_1$-$C_4$, halogen, a cyano group, a $-SO_3H$ group, a carboxyalkyl group $-COOR_5$, where $R_9$ has the same meaning as $R_6$ and where, when $R_1$, $R_2$ and $R_3$ are the same, they cannot be hydrogen, said use based on the surprising finding that the previously defined compounds are endowed with the capacity to modulate the activity or the content of plant proteolytic enzymes.

Preferably, in the above mentioned compounds, the substituents $R_1$, $R_2$ and $R_3$ being the same or different are selected from the group consisting of: hydrogen, alkyl $C_2$-$C_4$, $CH_2OR_4$ where $R_4$ is selected from the group consisting of: hydrogen, $-(CH_2CH_2O)_n-R_5$, in which n is an integer from 1 to 2 and $R_5$ is selected from the group consisting of: hydrogen, alkyl $C_1$-$C_4$, benzyl, aryl non substituted or substituted by: alkyl $C_1$-$C_3$, and where, when $R_1$, $R_2$ and $R_3$ are the same, they can never be hydrogen.

Still more preferably in such compounds of formula I, the substituents $R_1$, $R_2$ and $R_3$ being the same or different, are selected from the group consisting of: hydrogen, propyl, $CH_2OR_4$ where $R_4$ is $-(CH_2CH_2O)_2-R_5$ and $R_5$ is selected from the group consisting of: alkyl $C_2$-$C_4$, phenyl, toluoyl and where, when $R_1$, $R_2$ and $R_3$ are the same, they can never be hydrogen. Still more preferably such compounds correspond to piperonyl-butoxide (PBO) or 5-[[2-(2-Butoxyethoxy)ethoxy]methyl]-6-propyl-1,3-benzodioxole, of formula (II):

(II)

For simplicity we will make reference in the following text, only to the compound piperonyl-butoxide known by the abbreviation PBO or the term "benzodioxole derivatives", being understood that with this abbreviation and with this term is intended to refer in the present application, to all the compounds of general formula I, comprising the preferred substituents.

For the purpose of the present invention the terms proteases, proteinases or peptidases are used in an equivalent manner and are intended to refer to the peptidic hydrolases, denominated for simplicity proteolytic enzymes or proteases over the course of the present description, i.e. to enzymes with hydrolytic activity towards peptide or amidic bonds independently of their position, therefore either when they are internal to the polypeptide chain, or at the N- or C-terminal ends. According to this definition therefore, both endopeptidases type enzymes, and exopeptidases, such as the aminopeptidases or carboxypeptidases which hydrolyse the peptide bonds liberating single amino acids sequentially from the N- or C-terminal ends are comprised within the definition of proteolytic enzymes.

The proteolytic enzymes on which PBO exherts its regulatory activity, are preferably selected from the group consisting of: carboxypeptidases, aminopeptidases, dipeptidases, endopeptidases, wherein the endopeptidases are preferably selected from the group consisting of: serine proteases, cystein proteases, cathepsins, metallo-endopeptidases; the cystein proteases are preferably selected from the group consisting of: bromelain, calpain, ficin, papain, chymopapain.

The regulation of proteolytic activity in plants, for example through the activation of specific inhibitors has a predominantly defensive role in comparison to the proteases of insects and pathogenic micro-organisms. In the case of lesions produced by mechanical or biological means, protease inhibitors are synthesised de novo contributing to the defence strategy of the plant.

The modulatory potential of the inhibitors on the endogenous proteases could be modest in seeds and tends to disappear during germination; an important role has been attributed to the inhibitors during seed maturation to prevent protein degradation during the accumulation phase. Therefore according to further object, the invention comprises as a further embodiment the PBO proteolytic modulation activity on seeds; according to a further embodiment PBO is also useful to determine the activation of plant's defensive pathways in the case of wounds or lesions allowing the regulation of general tissue growth.

A further advantage of the novel activity on plant cell proteolytic activity herein described is the regulation of the production, of the maturation or of the degradation, or in other words of the turn-over of endogenous proteinaceous substances, for example those with natural insecticide or fungicide functions or with tissue repair functions. This mechanism may help in potentiating the natural response of the plant cell towards possible parasitic aggression, or towards externally derived stresses.

An example of substances endowed with fungicide activity, is described in Leah et al. J. Biol. Chem., 1991, 266:1564-1573 and is non extensively enlisted herein: Ribosome Inactivating Proteins (RIP), which have specificity for only distantly correlated ribosomes, such as fungi, but not for plant ribosomes, or the chitinases and the (1-3)-β-glucanases, which interfere with the synthesis of the cell walls of the fungus. Other substances produced by the plant in the form of inactive protein precursors, and having defensive functions against bacteria and fungi in their mature forms, are thionines, described for example in Bohlmann H. Critical Reviews in Plant Sciences, 1994, 13:1-16.

Treatment with PBO according to the novel use herein described is carried out as known to the skilled man on alt plant types, concentrating on the air exposed areas of the plant, and in particular on the leaves. The treatment can also be performed on seeds. In its preferred embodiment the treatment is preferably carried out on transgenic plants selected from the group consisting of: cotton, maize, potato, tomato and soya. According to this preferred embodiment, the invention refers to the use of benzodioxole derivatives as modulators of the proteolytic activity in plants transgenic for the insertion of a transgene encoding a protein.

The plant proteolytic activity variation obtained after treatment with PBO, has a differential effect depending on the system considered as it may allows to increase or even to reduce the availability of a protein, or of a protein in its active conformation. It is known that a steady state level is the result of the rate of protein degradation and production. However proteolysis is also known as a mechanism for protein activation. As a result, the new use allows an increase in the natural or induced defences of the plant towards parasitic infection or external attacks. Accordingly, a further and preferred embodiment of the invention is the regulation of transgenically expressed protein levels through the modulation of the proteolytic activity within a plant cell. Particularly preferred are plants transgenic for one of the *Bacillus thuringiensis* toxins.

In particular, in the case of plants transgenic for the *Bacillus thuringiensis* Bt toxin gene, the possibility of controlling the mechanism of proteolysis is extremely important both to control the activity of the transgenic toxin or to regulate its production.

It is however to be noted that this preferred embodiment of the invention is not limited to a single production or activation mechanism on the transgenic protein, but extends to all the mechanisms activated by PBO through a direct or indirect effect (such as through protease inhibitors) on proteolytic enzymes. An increase in the levels of proteolytic enzymes can be monitored by direct or indirect assays. Among the indirect assays the activity of proteases on various endogenous or exogenous substrates can be measured according to methods well known in the art.

In the case of transgenic plants, the transgene encodes one of the Cry protein of *Bacillus thuringiensis* and even more preferably for a protein selected from the group consisting of: CryI, Cry II, Cry III, Cry IV, in particular CryIA (a), (b) or (c). According to a particularly preferred embodiment the plant is cotton and the transgene encodes for the CryI toxin of *Bacillus thuringiensis*.

The authors of the present invention have additionally observed that in cotton transgenic for the Bt CryI protein, the amount of transgenic toxin after PBO treatment is higher than in transgenic untreated plants and this finding correlates with a loss in proteolytic activity in PBO-treated plants versus untreated, during a period of at least 100 days.

Hence the use of benzodioxole derivatives of formula I as proteolytic modulators is particularly advantageous in transgenic plants, preferably selected from the group consisting of: cotton, maize, tomato, potato or soya preferably when they are transgenic for Bt-toxin, still more preferably for the Cry I toxin, for inhibiting the proteolytic mechanisms directly or indirectly modifying the expression of the transgenic (i.e. inactivating or reducing) Bt toxin in the plant cell. Particularly preferred is the PBO treatment of cotton transgenic for one of the *Bacillus thuringiensis* toxins.

The levels of Bt toxin in plants are measured as known in the field, for example with immunoenzymatic assays carried out with antibodies specific for the Bt toxin. Alternatively, quantities of Bt toxin less than the useful limits can be estimated by directly measuring the lack of mortality in the parasitic insects in the field or in the laboratory.

According to an additional embodiment, the invention provides a process to regulate the proteolytic activity in plants, preferably to inhibit at least partially the proteolytic activity of a plant, comprising essentially the treatment of the plants with PBO or its derivatives or with the compositions comprising PBO as the active ingredient, in a way such that the concentration of the active ingredient is comprised from 50 to 800 grams/hectare, more preferably from 100 to 400 grams/hectare, even more preferably from 200 to 350 grams/hectare. The process according to the invention is preferably repeated up to three times per vegetative cycle and even more preferably is carried out at the end of the vegetative cycle. This preferred aspect is of particular relevance when the plant is transgenic and in particular when such plant, preferably cotton, maize, tomato, potato and soya, is transgenic for the Cry toxin of *Bacillus thuringiensis*. As a matter of fact the modulatory activity of PBO is observed few hours after the treatment up to few days, during different phases of the plant growth cycle.

The modulation of protease activity by PBO in plants is preferably a negative modulation, through a direct inhibition of PBO on the enzyme, or through an indirect effect such as, for example, through the activation of protease inhibitors or the de novo synthesis of specific protease inhibitors.

Treatment with PBO is conveniently carried out using compositions with appropriate excipients or emulsifiers. Therefore according to a further aspect the invention relates to the use of compositions containing the benzodioxole derivatives of formula I as the active ingredient, or the preferred embodiments thereof, such as PBO, in combination with appropriate emulsifiers or excipients and optionally with photoprotector compounds, as modulators of the activity or the content of proteolytic enzymes in plants. The emulsifiers used are selected from the group consisting of: calcium salts of alkylarylsulphonic acids, polyglycol esters of fatty acids, alkylarylpolyglycol ethers, polyglycol ethers of fatty alcohols, ethylene oxide-propylene oxide condensation products, alkyl polyethers, sorbitanic fatty acid esters, polyoxyethylen-sorbitanic fatty acid esters, polyoxyethylene sorbitanic esters. Particularly preferred are the emulsifiers selected from the group consisting of: alkylarylpolyglycol ethers and calcium salts of alkylarylsulfonic acid. The emulsifiers are present at a minimum concentration of 2% (w/w).

The concentration of PBO in the compositions with emulsifiers or excipients is comprised from 1 to 98% (w/w), preferably from 20 to 95%, even more preferably from 50 to 90%.

For the purposes herein the mixture of active ingredients in combination with the appropriate excipients or emulsifiers is denominated "concentrate". To the concentrate is optionally added a protective agent against photo oxidation (photoprotectors) selected from the class of compounds consisting of: benzotriazoles, benzophenones, and sterically hindered amines, in concentrations comprised from 0.1% to 10%, preferably from 0.5% to 8%, even more preferably from 1% to 5% in weight of the concentrate.

Amongst benzotriazoles, compounds are selected from the group consisting of: 2-(2'-hydroxy-5-t-octylphenyl)benzotriazole and 2-(2'-hydroxy-3',5'-di-t-butylphenyl)-5-chlorobenzotriazole.

Amongst benzophenones, compounds are selected from the group consisting of: 2-hydroxy-4-methoxy benzophenone, 2-hydroxy-4-octyloxy benzophenone, 2'-dihydroxy-4, 4'-dimethoxybenzophenone.

Amongst sterically hindered amines, compounds are selected from the group consisting of: di(2,2,6,6-tetramethyl-4-piperinidyl) sebacate; di(1,2,2,6,6-pentamethyl-4-piperidinyl) sebacate; alpha-[[6-[[4,6-bis(dibutylamino)-1,3,5-triazin-2-yl](2,2,6,6-tetramethyl-4-piperidinyl)amino] hexyl](2,2,6,6-tetramethyl-4-piperidinyl)amino]-omega-[4, 6-bis(dibutylamino)-1,3,5-triazin-2-yl]-poly[[6-[butyl(2,2, 6,6-tetramethyl-4-piperidinyl)amino]-1,3,5-triazin-2,4-diyl] [2,2,6,6-tetramethyl-4-piperidinyl)imino]-1,6-hexandiyl[2, 2,6,6-tetramethyl-4-piperidinyl)imino]; polymer of dimethylsuccinate with 4-hydroxy-2,2,6,6-tetramethyl-1-piperidinethanol; polymer of N,N' di(2,2,6,6-tetramethyl-4-piperinidyl)-1,6-hexanediamine with 2,4,6 trichloro-1,3,5-triazine and 1,1,3,3-tetramethylbutylamine; polymethylpropyl-3-oxy(4((2,2,6,6-tetramethyl)piperidinyl siloxane; 1,3,5-triazine-2,4,6,-triamine, N,N'''[1,2-ethanediyl di[[[4,6-bis[butyl (1,2,2,6,6-pentamethyl-4-piperidinyl)amino]-1,3,5-triazine-2il]imino]-3,1-propano diyl]]-di[N',N''-dibutyl N',N''-bis(1,2,2,6,6-pentamethyl-4-piperidinyle)] or the following mixture: mixture of the polymer of dimethylsuccinate with 4-hydroxy-2,2,6,6-tetramethyl-1-piperidin ethanol and the polymer of N,N' di(2,2,6,6-tetramethyl-4-piperinidyl)-1,6-hexanediamine with 2,4,6 trichloro-1,3,5-triazine and 1,1,3,3-tetramethylbutylamine.

Particularly preferred are benzophenones, even more preferably 2-hydroxy-4-methoxy benzophenone and 2-hydroxy-4-octyloxy benzofenone, and amongst sterically hindered amines, preferred compounds are di(2,2,6,6-tetramethyl-4-piperinidyl) sebacate and di(1,2,2,6,6-pentamethyl-4-piperidinyl) sebacate.

The concentrate, optionally containing the photoprotective agent, is emulsionable and is therefore mixed with water so as to obtain the appropriate solutions to be nebulised preferably by field spraying such that the concentration of PBO is comprised from 50 to 800 grams/hectare, preferably from 100 to 400 grams/hectare, even more preferably from 200 to 350 grams/hectare. Every treatment cycle in the field can be composed of one up to three treatments per vegetative cycle.

The invention will be now better detailed in the following experimental examples, which do not represent any limitation thereof.

EXPERIMENTAL PART

Example 1

In Vitro Inhibition of Cysteinic Endopeptidases by Piperonyl Butoxide

The assays were carried out in the reverse-micelles assay dispersed in organic solvent, described by Walde et al. in Eur.

J. Biochem., 1988, 173:401-409, and already reported in the literature in kinetic studies of the inhibition of trypsin with natural and synthetic inhibitors. Such an assay was adapted to the following purified plant enzymes: papain, ficin and bromelain (Sigma catalogue No: P4762, F4125, B5144 respectively) in the presence of substrate CBZ (L lysine-p-nitrophenyl ester, Sigma catalogue No C3637), and carried out respectively with Wo (molar ratio water/surfactant or $H_2O$/AOT)=23, 25, 28.

The enzyme assay on reverse-micelle has been already described in the literature for the enzyme trypsin and was adapted to different enzymes. These values were obtained by vigorously mixing, in a quartz spectrophotometry cell, 1 ml of 50 mM AOT-ISO with appropriate volumes of protease and different buffer solutions, respectively MES (2-[N-morpholino]ethanesulfonic acid) for the enzyme papain, HEPES (N-[2-Hydroxyethyl]piperazine-N'-[2-ethanesulfonic acid]) for the enzyme ficin and acetate for the enzyme bromelain. When the solution was completely transparent and apparently homogeneous, it was adjusted thermostatically to 30° C. To this solution was added an appropriate volume of substrate CBZ (dissolved in acetonitrile/$H_2O$, 80:20 (v/v) at a concentration of 15 mM) and following further agitation (the solution returned to being transparent), the change in absorbance was measured (Dabs) at 340 nm with a Cary 219 spectrophotometer. The assay conditions in summary, were the following:

| Papain: | |
|---|---|
| AOT-ISO: | 50 mM (bis 2-etylhexyl sodium sulfosuccinate- isooctane) |
| Wo: | 23 |
| buffer: | 50 mM MES pH 6.2 containing 2.5 mM cystein, |
| temperature: | 30° C. |
| substrate: | $1.5 \times 10^{-4}$ M and $6 \times 10^{-5}$ M CBZ (L lysine-p-nitrophenyl ester, Sigma) |
| papain: | 2 mg/ml |
| PBO (when present): | from $4.87 \times 10^{-4}$ M to $5.9 \times 10^{-3}$ M |
| Ficin: | |
| AOT-ISO: | 50 mM (bis2-ethylhexyl sodium sulfosuccinate- isooctane) |
| Wo: | 25 |
| buffer: | 50 mM HEPES pH 7.1 containing 2.5 mM L-cystein, |
| temperature: | 30° C. |
| substrate: | $1.5 \times 10^{-4}$ M and $6 \times 10^{-5}$ M CBZ (L lysine-p-nitrophenyl ester, Sigma) |
| ficin: | 1.7 mg/ml |
| PBO (when present): | from $4.87 \times 10^{-4}$ M to $5.9 \times 10^{-3}$ M |
| Bromelain: | |
| AOT-ISO: | 50 mM (bis2-ethylhexyl sodium sulfosuccinate- isooctane) |
| Wo: | 28 |
| buffer: | 10 mM Acetate, pH 4.6 containing 1 mM L-cystein |
| temperature: | 30° C. |
| substrate: | $1.5 \times 10^{-4}$ M and $6 \times 10^{-5}$ M CBZ (L lysine-p-nitrophenyl ester, Sigma) |
| bromelain: | 2 mg/ml |
| PBO (when present): | from $4.87 \times 10^{-4}$ M to $5.9 \times 10^{-3}$ M. |

Figure 1:
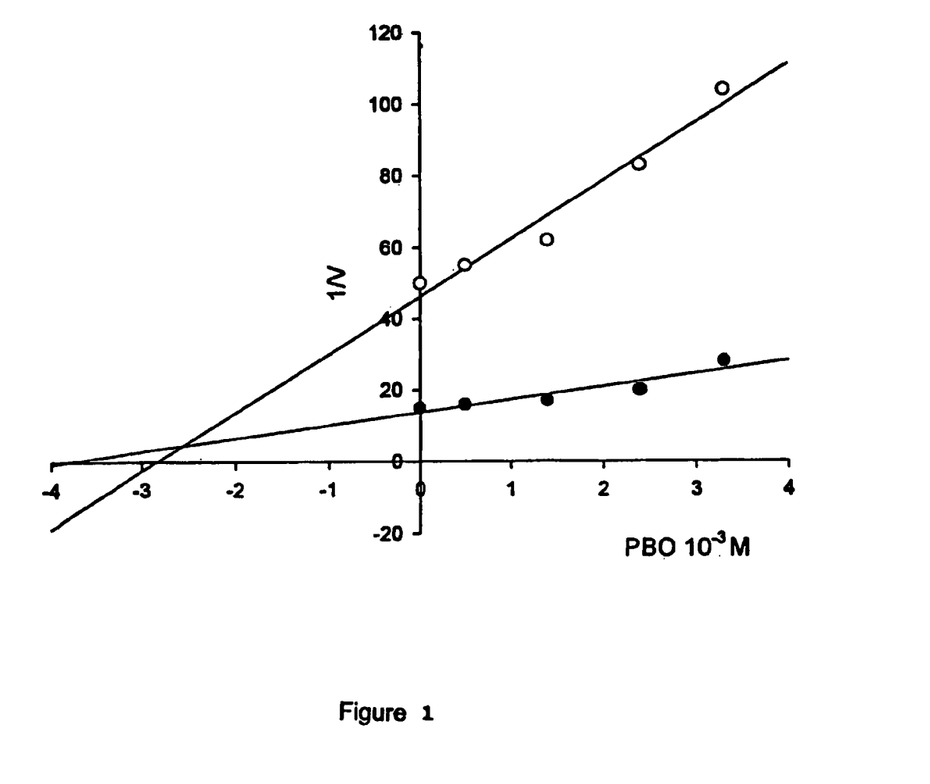
FIG. 1. Graphical representation of the inhibition of increasing concentrations of PBO on the activity of the enzyme papain by Dixon-plot. From the Dixon-plot obtained at two different substrate concentrations (CBZ: L lysine-p-nitrophenyl ester), used at $1.5 \times 10^{-4}$ M (full circle -●-) and $6 \times 10^{-5}$ M (empty circle -○-) respectively, it is possible to calculate the inhibition constant ($K_I$) of PBO on the enzyme papain, which as equal to $2.6 \times 10^{-4}$M. In addition, from the diagram it is possible to evaluate the $IC_{50}$ equal to $2 \times 10^{-4}$M.
Figure 2:
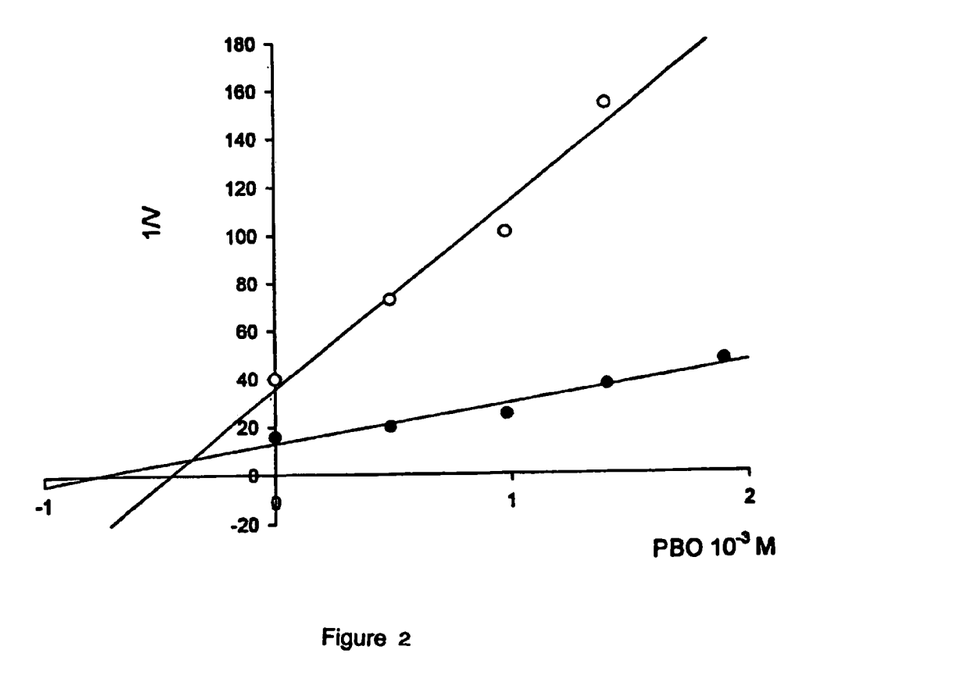
FIG. 2. Graphical representation of the inhibition of increasing concentrations of PBO on the activity of the enzyme ficin by Dixon-plot.
Figure 3:
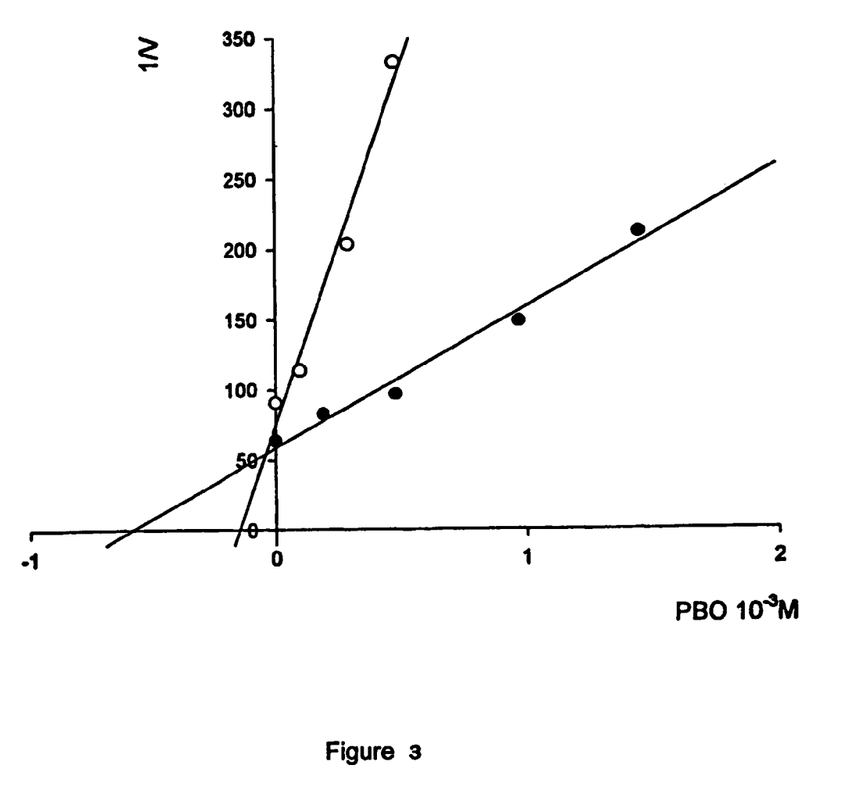
FIG. 3. Graphical representation of the inhibition of increasing concentrations of PBO on the activity of the enzyme bromelain by Dixon-plot.

The experimental data obtained are represented graphically in the form of Dixon-plot (described for example in: "Quantitative Problems in Biochemistry", E A. Dawes, $5^{th}$ ed. 1972 Baltimore, The Williams and Wilkins Company), in the FIGS. 1, 2 and 3. Such a graphical representation allows the calculation of the Ki values (inhibition constant) obtained for PBO respectively on papain: $2.6 \times 10^{-3}$ M, on ficin: $4.5 \times 10^{-4}$ M and on bromelain: $1 \times 10^{-4}$ M, therefore indicating that the inhibitory effect of PBO is higher on bromelain. The test results, obtained at non saturating substrate concentrations, indicate that, under these conditions, PBO inhibits all the proteases tested. In particular from the Dixon plots presented in FIGS. 1-3 it is possible to evaluate the $IC_{50}$ of PBO which on the papain system is equal to $2 \times 10^{-3}$ M, on the enzyme ficin it is equal to $0.8 \times 10^{-3}$ M and on the enzyme bromelain is equal to $0.4 \times 10^{-3}$ M.

Example 2

Inhibition of Bromelain by PBO

The assay was carried out as described in Heinrikson & Kezdy, 1976, Methods in Enzymol. 45, p. 740. The conditions are summarised briefly herein: 50 µg of bromelain was mixed with variable quantities of Na CBZ-L-lysine p-nitrophenyl ester substrate in 3 ml of 10 mM acetate buffer pH 4.6 containing KCl (0.1 M) and L-cystein (1 mM). The changes in the initial velocities of the reaction were measured by the changes in absorbance at 340 nm/min, in the presence of a 1% solution of PBO in $H_2O$ in two different experiments.

The results are presented in table 1.

TABLE 1

The effect of 1% PBO on the activity of bromelain.

| Substrate conc. | control | test 1 | test 2 | Mean (% contr.) |
|---|---|---|---|---|
| 24 µM | 0.0199 | 0.0141 | 0.0130 | 0.0136 (68%) |
| 48 µM | 0.0297 | 0.0243 | 0.0297 | 0.0270 (68%) |
| 96 µM | 0.0623 | 0.0518 | 0.0461 | 0.0490 (78%) |

The data indicate that 1% PBO has an inhibitory effect on bromelain which for substrate concentrations comprised of between 20-24 µM and 48-50 µM, is variable from 65 to 80%.

The experiment was repeated using increasing concentrations of PBO and a fixed substrate concentration (240 µM). The data are reported in table 2.

TABLE 2

Effect of increasing quantities of PBO on the activity of the enzyme bromelain

| % PBO (w/w) | Exp. 1 | Exp. 2 | Exp. 3 |
|---|---|---|---|
| | Initial velocity (% of control) | | |
| 0 | 0.1382 | 0.1221 | 0.1051 |
| 0.334 | 0.1306 (95%) | 0.1197 (98%) | 0.1029 |
| 0.5 | 0.1252 (91%) | — | — |
| 0.667 | — | 0.1079 (88%) | — |
| 1 | 0.1194 (86%) | 0.1057 (86%) | — |
| 1.334 | — | 0.1029 (84%) | — |
| 1.667 | — | 0.0927 (76%) | — |

From the data in table 2 it may be observed that PBO at concentration values higher than 0.5% has an inhibitory activity of the proteolytic enzyme bromelain. This effect is concentration dependent. The degree of the inhibition is in agreement with the data obtained in the previous examples.

Example 3

Effect of PBO on Carboxypeptidase and Endopeptidase in Cotton Seedlings

With the aim to evaluate the effect of PBO on the endogenous plant enzymatic system in cotton in vitro assays were carried out using acetonic powders got from treated (PBO) and untreated freeze dried seed sprouts, without the addition of any specific exogenous substrate. The basic idea was to "freeze" the physiologic protein hydrolysis enzymatic activity and to re-establish the process simply solubilizing the proteolytic enzymatic system in suitable buffers, which were 0.1 M phosphate pH 6.5 and 0.1 M tris-HCl pH 7.7, for evaluating both the carboxypeptidase and the endopeptidase activities according to the method described by Hile et al. 1972; Funkhouser et al. 1980.

Materials and Methods

Cotton seeds (cv. Carmela) were obtained from "Semillas Battle", Barcelona (E).

Germination Conditions

The seeds were previously rinsed in tap water and then imbibed with aeration in distilled water over night (Funkhouser, E. A. et al., *Z. Pflanzenphysiol.*, 1980, 100, 319-324). After this process, seeds were planted in settled and sterile sand and then watered with distilled water (untreated seeds) and with the same volume of a micro-suspension of saturated PBO (1% w/v) (treated seeds). The plastic boxes containing seeds were covered by a plastic film and placed in a germinator in the dark for 4 days at 30° C. as described in Hile, J. N. and Dure, L. S. *J. Biol. Chem.*, 1972, 247: 5034-5040.

Freeze Drying

The cotton sprouts of 4 days were collected and frozen in liquid nitrogen and freeze dried (Hile et al. 1972). After this process, the material was crushed in a pestle and freed from fibrous material and settled up to obtain a pretty homogeneous meal of about 0.5 mesh.

Acetonic Powders Preparation

The meals were defatted using n-hexane (1:10 w/v) at room temperature and then treated with acetone at −20° C. to remove pigments and polyphenolic compounds, in this case mainly gossypol. The powders obtained were stored in a dry box at room temperature.

Carboxypeptidase Assay

The acetonic powder (30 mg) was suspended in buffer (4 ml) and incubated at 37° C. for 30, 60, 90, 120 minutes. The proteolysis was stopped adding 1 ml of 12% trichloroacetic acid. In this case, the buffer used was 0.1 M phosphate pH 6.5 (Hile et al. 1972). The control was a suspension of the same sample prepared in the same way but, in this case, it was immediately deactivated, adding 1 ml of trichloroacetic acid. The trials with treated and untreated samples were carried out at the same time.

Photometric Analysis

Proteins were precipitated with trichloroacetic acid and then removed by filtration, before with Whatman paper n. 4 and then by micro-filtration (Orange Scientific Braine l'Alleud, Belgium (Ø0.2 µm)). Finally, the hydrolyzed protein samples were analyzed as clear solutions by determining the absorbance at 280 nm in a quartz cuvette.

Each series of analysis was performed twice. The comparison between the values of carboxypeptidase activity of treated and untreated samples was done using the average value of each series of analysis.

Figure 4:
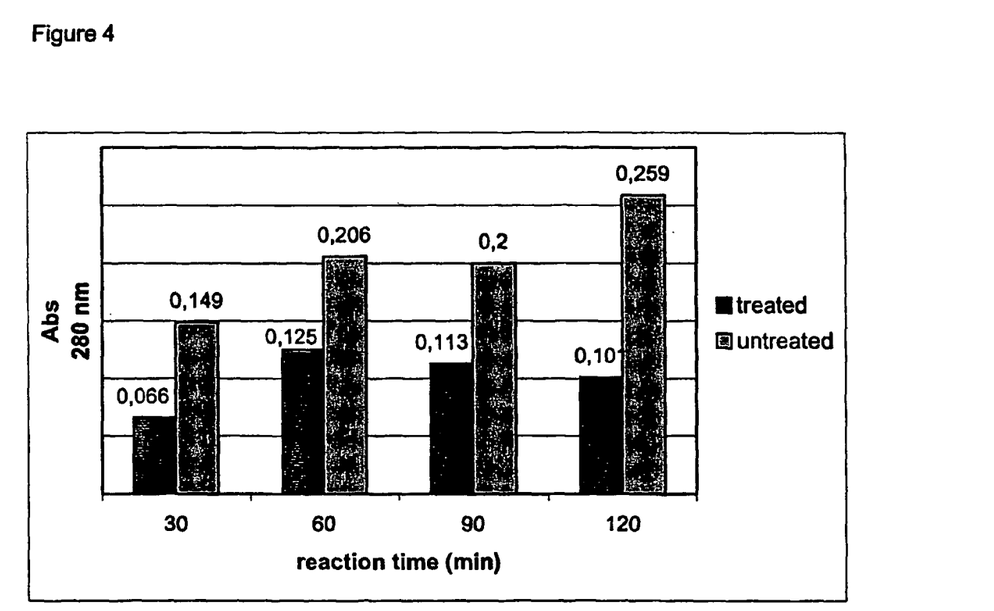
FIG. 4. Carboxypeptidase activity in cotton sprouts after 4 day of germination.

From the data shown in FIG. 4 it may be inferred that the proteolytic activity related to carboxypeptidase in treated samples is lower than in the untreated ones.

In Table 3 the percentage of these differences is also reported.

TABLE 3

Carboxypeptidase activity of treated and untreated cotton sprouts at the $4^{th}$ day of germination.

| | Untreated Cotton Sprouts | | | | PBO Treated Cotton Sprouts | | | | | |
|---|---|---|---|---|---|---|---|---|---|---|
| Exp. n° Time | 1 | 2 | Mean | Activity (U) | 1 | 2 | Mean | Activity (U) | Δ U | % |
| 0 | 0.759 | 0.695 | 0.727 | | 0.632 | 0.729 | 0.68 | — | | |
| 30' | 0.894 | 0.858 | 0.876 | 0.149 | 0.730 | 0.763 | 0.746 | 0.066 | 0.083 | 55.7 |
| 60' | 0.925 | 0.942 | 0.933 | 0.206 | 0.752 | 0.858 | 0.805 | 0.125 | 0.081 | 39.3 |
| 90' | 0.988 | 0.956 | 0.927 | 0.200 | 0.880 | 0.838 | 0.859 | 0.113 | 0.087 | 43.5 |
| 120' | 0.943 | 1.030 | 0.986 | 0.259 | 0.775 | 0.787 | 0.781 | 0.101 | 0.158 | 61.0 |

Endopeptidase Assay

The acetonic powder (30 mg) was suspended in buffer (4 ml) and incubated at 37° C. for 15', 30, 60, 90, 120 minutes. The proteolysis was stopped adding 1 ml of 12% trichloroacetic acid. In this case the buffer used was 0.1 M phosphate pH 7.7 (Funkhouser et al. 1980). The control was a suspension of the same sample prepared in the same way but was immediately deactivated, adding up 1 ml of trichloroacetic acid. The trials with treated and untreated samples were carried out at the same time.

Photometric Analysis

Proteins were precipitated with trichloroacetic acid and then removed by filtration, before with Whatman paper n. 4 and then by micro-filtration (Orange Scientific Braine l'Alleud, Belgium (Ø0.2 µm)). Finally, the hydrolyzed protein samples were analyzed as clear solutions by determining the absorbance at 280 nm in a quartz cuvette.

Figure 5:
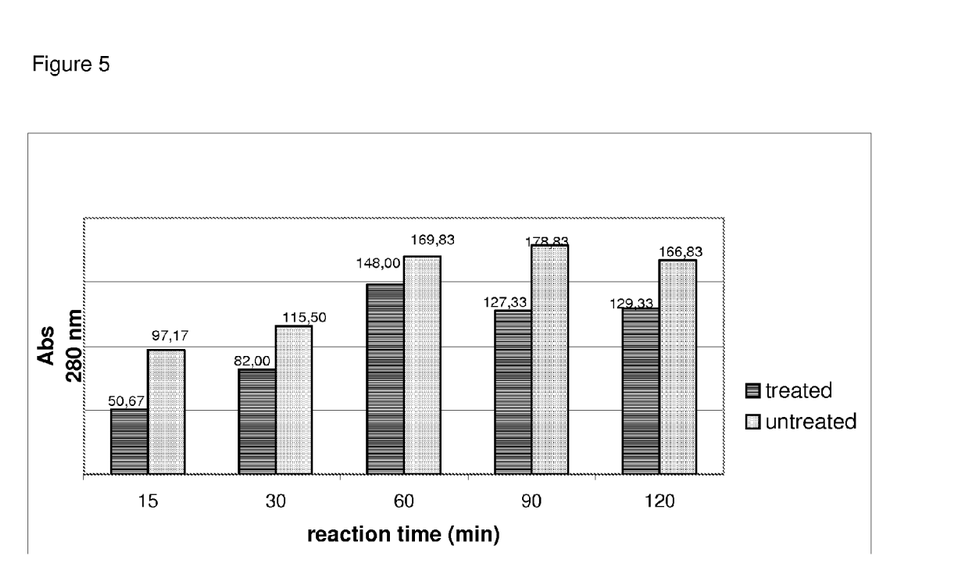
FIG. 5. Endopeptidase activity in cotton sprouts after 4 day of germination.
Figure 6:
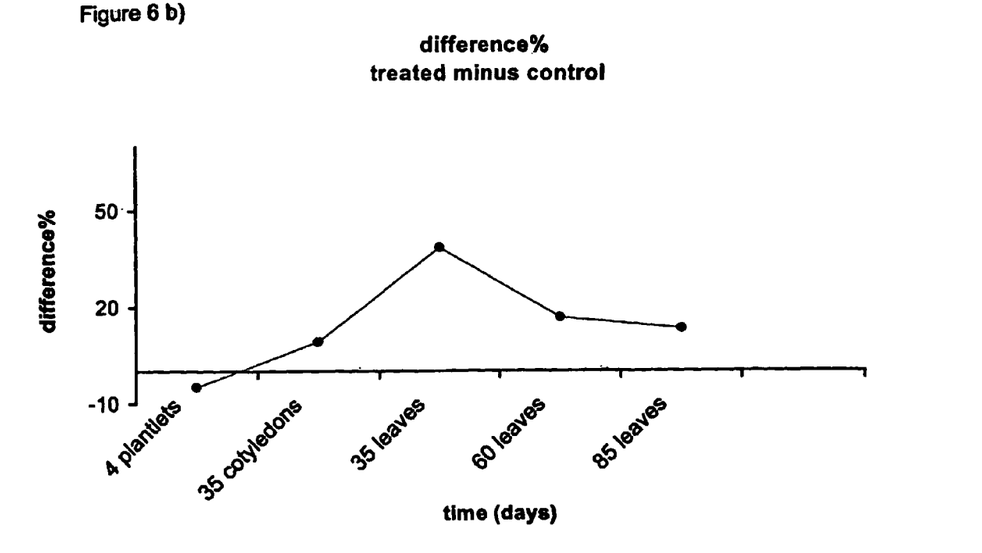
FIG. 6. Bt content in PBO treated vs PBO untreated cotton plants.
Figure 6A:
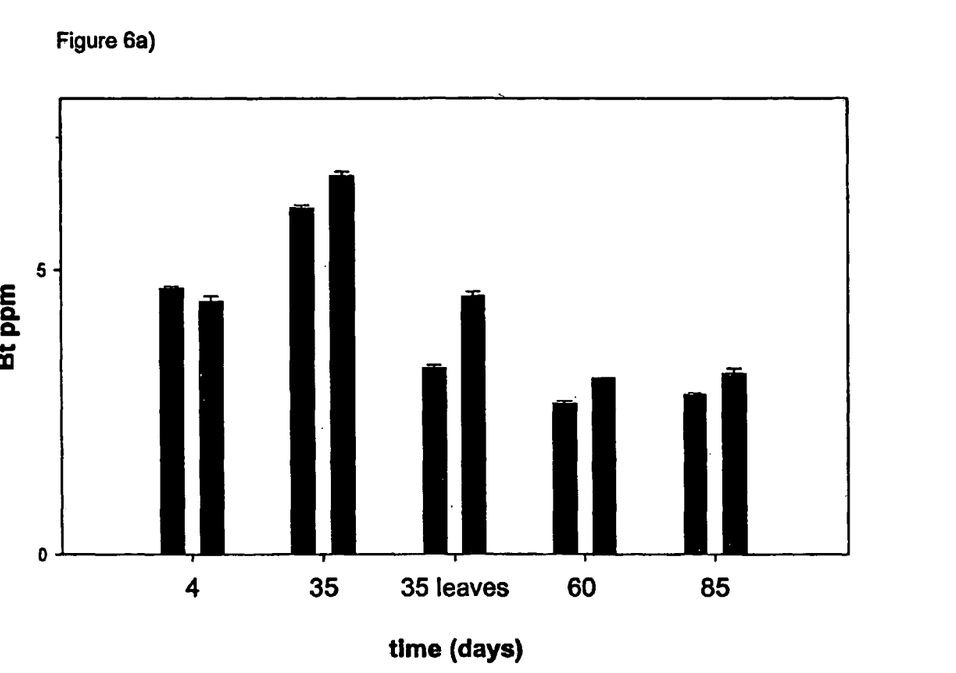

Each series of analysis was performed threefold. The comparison between the values of endopeptidase activity of treated and untreated samples was done using the average value of each series of analysis. As it is possible to see in FIG. 5, also the endopeptidase activity in PBO treated cotton sprouts is lower than in the untreated ones. In Table 4 the percentage of these differences is also reported.

TABLE 4

Endopeptidase activity in PBO treated and untreated cotton sprouts at 4 days of germination.

| | Untreated Cotton Sprouts | | | | | Cotton Sprouts Treated with PBO | | | | | | |
|---|---|---|---|---|---|---|---|---|---|---|---|---|
| Time | 1 | 2 | 3 | Mean | Activity (U × 10³) | 1 | 2 | 3 | Mean | Activity (U × 10³) | Δ U | % |
| 0 | 850.00 | 845.00 | | 847.50 | == | 821.00 | 897.00 | 886.00 | 868.00 | == | == | == |
| 15' | 953.00 | 956.00 | 925.00 | 944.67 | 97.17 | 965.00 | 876.00 | 915.00 | 918.67 | 50.67 | 46.50 | 47.86 |
| 30' | 972.00 | 965.00 | 952.00 | 963.00 | 115.50 | 965.00 | 935.00 | 950.00 | 950.00 | 82.00 | 33.50 | 29.00 |
| 60' | 1008.00 | 1014.00 | 1030.00 | 1017.33 | 169.83 | 1038.00 | 1038.00 | 972.00 | 1016.00 | 148.00 | 21.83 | 12.86 |
| 90' | 1031.00 | 1045.00 | 1003.00 | 1026.33 | 178.83 | 1015.00 | 991.00 | 980.00 | 995.33 | 127.33 | 51.50 | 28.80 |
| 120' | 1021.00 | 985.00 | 1037.00 | 1014.33 | 166.83 | 1017.00 | 960.00 | 1015.00 | 997.33 | 129.33 | 37.50 | 22.48 |

Example 4

Effect of PBO on Bt-Toxin Content in Transgenic Cotton Plant Samples

With the aim to find the correlation between Bt toxin levels and the effect of the PBO treatment on cotton plants, the Bt toxin concentration was measured in Bt transgenic cotton plant samples (cv.SicalaV2i) treated with PBO or untreated (the control).

The assay was carried out on samples collected at different plant development stages, which were: 4, 35, 60, 85 days after sowing.

Materials and Methods.

In order to determine the Bt toxin concentration in PBO treated or untreated cotton samples, a specific ELISA assay was used. The ELISA Cry1Ab/Cry1Ac Plate Kit was obtained from Envirologix (Portland, Maine—USA). The assay was performed according to the Envirologix protocol with the following modifications:

1. The cotton freeze-dried powder got from leaf or cotyledon tissues was used instead of the fresh and whole leaf tissue.
2. The Bt toxin extraction from the cotton freeze-dried powder was done with a sample/buffer ratio of 1:25 (w/v).
3. The extraction was made leaving the sample in the buffer for at least 4 hours at room temperature, instead of using the Envirologix Disposable Tissue Extractor. The extract was then clarified by centrifugation at 5,000×g for 5 min at room temperature.

FIG. 6*a* shows the Bt concentrations in PBO treated or untreated cotton plant samples at the plant development stages reported above. In FIG. 6 and in table is also shown that there is a significant lower Bt content in PBO-treated samples at 35, 60, 85 days after planting, whereas no difference was found at 4 days. FIG. 6*b* shows the difference in percentage between PBO-treated and untreated cotton plant samples.

In table 5 are summarized the results obtained with the described assay.

TABLE 5

Bt content and differences between PBO treated with and untreated samples in transgenic cotton

| | Cry1Ac ppm | | | |
|---|---|---|---|---|
| Growth stage days (tissue) | cv V2i untreated | cv V2i PBO treated | Δ: treated − control | %: treated − control |
| 4 (plantlets) | 46.86 | 44.60 | −2.26 | −4.823 |
| 35 (cotyledons) | 60.99 | 66.57 | 5.58 | 9.149 |
| 35 (leaves) | 32.85 | 45.45 | 12.6 | 38.356 |
| 60 (leaves) | 26.64 | 31.07 | 4.43 | 16.629 |
| 85 (leaves) | 28.18 | 31.91 | 3.73 | 13.236 |

Δ: difference in values treated minus control (cv V2i untreated)

Example 5

Effect of PBO Treatment on Protease (Endoprotease) Activity in Cotton Plants at Different Growing Stages With the aim to evaluate the action of PBO on the proteolytic activity in cotton plants, the enzymatic activity was tested on samples of PBO treated and untreated cotton leaves (as control). The samples were collected at different development stages of plants, which were: 4, 0.35, 60 and 85 days after sowing. These samples were also analysed for determining the Bt content (as described in example 4). To this aim, the enzymatic activity was tested on crude freeze dried leaf extracts with two different assays: the Radial Diffusion Assay (RDA), in which a protein, such as the bovine gelatine, was used as a substrate to test the endopeptidase activity, and a photometric assay described in the next example, in which DL-BAPA was used as a substrate, to determine a general peptidase activity.

Materials and Methods

Plant Culture

Cotton seeds of the cv. Sicala V2i were previously rinsed in distilled water and then placed in equal number in suitable plastic boxes containing settled and sterile sand. Seeds were watered with equal volumes of distilled water and the culture boxes were then covered with a plastic film to avoid evaporation during germination, which was carried out in the dark for 4 days at 30° C. The seeds to be analysed after 4 days of germination were watered with distilled water or with an equal volume of a micro-suspension saturated of PBO (2% w/v). After 4 days, these sprouts were collected for testing, whereas the other sprouts were moved in suitable pots and located in the greenhouse at 24° C. during the day and 20° C. in the night.

Treatments

At fixed times of 4, 35, 60, 85 days after sowing, 10 plants fairly homogeneous for height were treated with a commercial PBO formulation (Endura) 2% (w/v). Treatments were given out vaporizing the diluted formulation on the plants taking care to treat both leaves sides.

Freeze Drying

Two days after each treatment, a sample of the treated plants, and the correspondent controls, were collected and all leaves were frozen in liquid nitrogen and freeze dried. After this process, the material was powdered in a pestle and then stored in a dry box at room temperature.

Extract Preparation

A powder aliquot, which represents each step of plant growth, of the treated and controls samples was extracted in two steps. The powder sample was extracted with buffer 0.1 M Tris-HCl pH 7.7 (1:20 w/v) using an Ultraturrax blender at 24,000×RPM for 2 min in a ice bath to avoid overheating. The extract was then clarified by centrifugation at 5,000×g at 10° C., for 20 min. The clear supernatant was collected and filtrated with Whatman paper no 4. The pellet was further extracted with the same procedure, with the exception that in this case the extraction ratio was 1:10 (w/v). Finally, the supernatants of the two extractions processes were joined and then concentrated 4-5 times by centrifugation at 3,000×g at 15° C. for 2 hours, using suitable concentrators (Amicon Inc. Beverly, Mass.—USA), fitted with a membrane of 10 κD cut off.

Protein Concentration

For each extract, the amount of soluble proteins was determined by the Biuret method and the enzymatic activity was then expressed as specific activity i.e. Units/mg soluble proteins.

RDA was performed as described in Santarius, K. and Ryan, C., Anal. Biochem., 1977, 77: 1-9 in Petri dishes containing bovine gelatine as substrate, dispersed in agar gel. Each dish contained 5 wells of which 4 were filled with suitable aliquots of concentrated cotton extracts, whereas one was filled with a bovine β-trypsin as standard solution (0.2 U/ml). The dishes were covered and sealed with a plastic film to avoid evaporation and then incubated at 37° C. for 16 hours.

The enzymatic activity in the protein-agar gel produced a clear radial diffusion zone around each circular wells, due to the bovine gelatine proteolysis against an opaque background.

The trypsin equivalents were calculated by measuring the radii of the clear zones produced by the plant extracts and compared to a standard curve obtained by a serial dilution of trypsin. Each dish contained a standard solution of trypsin that was used to plot a standard curve for each plate, thus the endopeptidase activity was expressed as units of trypsin equivalents.

Figure 7:
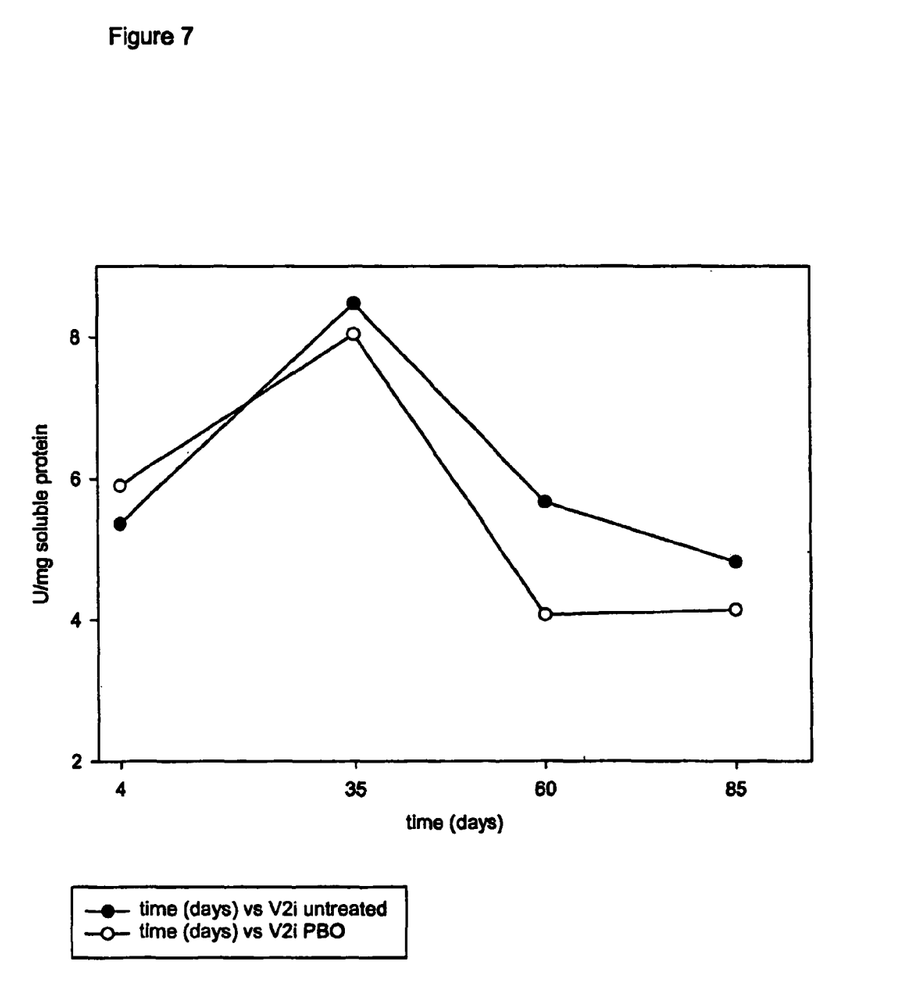

Each analysis was performed in quadruplicate. FIG. 7 shows the values of endopeptidase activity obtained with RDA of the treated and untreated cotton samples. This experiment points out that the commercial PBO formulation (Endura), especially at 35, 60, 85 days after sowing, significantly inhibited the endopeptidase activity in cotton leaves of Sicala V2i genotype. In table 6 are shown the differences between treated and untreated cotton samples as percentages.

TABLE 6

Endopeptidase activity of PBO treated and untreated samples by the RDA assay.

| | U/mg protein | | Difference % |
| --- | --- | --- | --- |
| Days after sowing | cv. V2i Bt untreated | cv. V2i Bt PBO | Treated minus untreated |
| 4 | 5.36 | 5.90 | 9.15 |
| 35 | 8.47 | 8.04 | −5.35 |
| 60 | 5.67 | 4.07 | −39.31 |
| 85 | 4.82 | 4.14 | −16.42 |

U = trypsin equivalents

The photometric assay was carried out as described in Erlanger, B. F. et al. Arch. Biochem., 1961, 95: 271-278. In the assay is measured the absorbance variation due to DL-BAPA hydrolysis at 410 nm. The assay was performed mixing directly in the cuvette 20 μl of cotton crude extract with 980 μl of DL-BAPA in buffer 0.1 M Tris-HCl pH 8.2. One peptidase unit was defined as the amount of the enzyme which produces one unit of absorbance variation (410 nm) per minute at pH 8.2 and 30° C.

Figure 8:
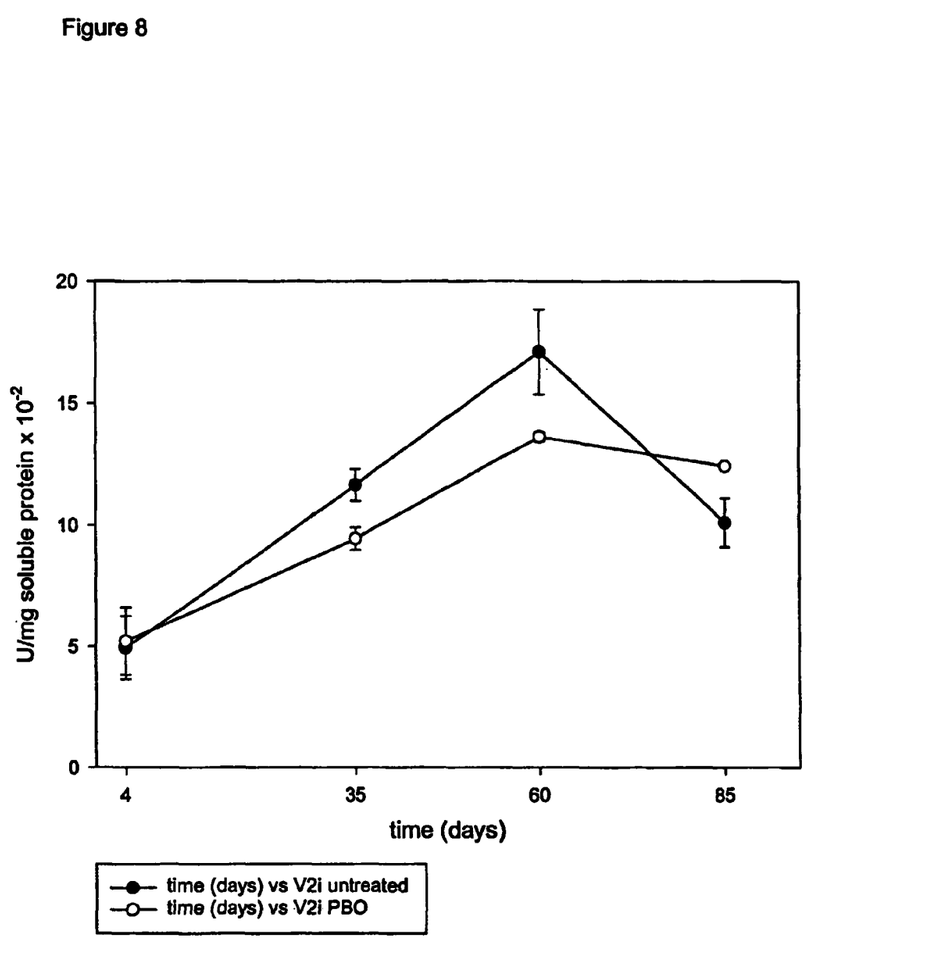

Each series of analysis was performed in duplicate or triplicate. FIG. 8 reports the values of peptidase activity in PBO treated and untreated cotton samples calculated as U/mg of soluble protein. In this figure is shown a maximum of peptidase activity around 60 days of development. At this time the treatment with commercial PBO formulation (Endura) shows a maximum significant inhibition of the proteolytic activity on the Sicala V2i cotton. Differences in the proteolytic activity are observed throughout the plant growing cycle by this assay in PBO treated vs untreated cotton plants. A statistically significant inhibition is observed during the most part of the plant growing cycle. Finally, in table 7 is shown the specific activities of peptidase of treated and untreated Sicala V2i cotton samples. In this table it is also reported the activity differences in percentage between the treated and untreated samples.

TABLE 7

Peptidase activity (U/mg of soluble protein) of PBO treated and untreated samples, in the photometric assay with DL-BAPA as substrate.

| | U/mg of soluble protein × $10^{-2}$ | | Difference % |
| --- | --- | --- | --- |
| Days after sowing | untreated cv. V2i Bt | PBO treated cv. V2i Bt | Treated minus untreated |
| 4 | 4.95 | 5.21 | 4.99 |
| 35 | 11.65 | 9.43 | −23.54 |
| 60 | 17.10 | 13.62 | −25.55 |
| 85 | 10.10 | 12.42 | 18.68 |

The invention claimed is:

1. A method consisting of treating plants with a benzodioxole derivative of formula I as the only active ingredient (I)

wherein $R_1$, $R_2$ and $R_3$, either the same or different, are selected from the group consisting of: hydrogen; alkyl $C_2$-$C_4$; and $CH_2OR_4$ where $R_4$ is selected from the group consisting of: hydrogen, and —$(CH_2CH_2O)_n$—$R_5$, in which n is an integer from 1 to 2 and $R_5$ is selected from the group consisting of: hydrogen, alkyl $C_1$-$C_4$, and benzyl, and where, when $R_1$, $R_2$ and $R_3$ are all the same, they can never be hydrogen, for modulating the activity or the content of proteolytic enzymes in plants transgenic for at least one *Bacillus thuringiensis* toxin.

2. The method according to claim 1 wherein $R_1$, $R_2$ and $R_3$ either the same or different are selected from the group consisting of: hydrogen, propyl, and $CH_2OR_4$ where $R_4$ is —$(CH_2CH_2O)_2$—$R_5$ and wherein in $R_5$ said alkyl is a $C_2$-$C_4$.

3. The method according to claim 2 wherein the benzodioxole derivative has formula II:

(II)

4. The method according to claim 1 wherein said proteolytic enzymes are selected from the group consisting of: carboxypeptidases, and endopeptidases.

5. The method according to claim 4 wherein said endopeptidases are selected from the group consisting of: serine proteases, cystein proteases, cathepsins, and metallo-endopeptidases.

6. The method according to claim 5 wherein said cystein proteases are selected from the group consisting of: bromelain, calpain, ficin, papain, and chymopapain.

7. The method according to claim 1 wherein said plants transgenic for at least one *Bacillus thuringiensis* toxin are selected from the group consisting of: soya, maize and cotton.

8. The method according to claim 1 wherein the at least one *Bacillus thuringiensis* toxin is a *Bacillus thuringiensis* Cry protein.

9. The method according to claim 8 wherein the Cry protein is selected from the group consisting of: CryI, Cry II, Cry III, and Cry IV.

10. The method according to claim 9 wherein said protein is the CryIA protein of subtype (a), (b) or (c).

11. The method according to claim 1 wherein said modulation is a negative modulation.

12. The method according to claim 1 wherein said benzodioxole derivatives are mixed with suitable emulsifiers.

13. The method according to claim 12 wherein said emulsifiers are selected from the group consisting of: calcium salts of alkylarylsulfonic acids, polyglycol esters of fatty acids, alkylarylpolyglycol ethers, polyglycol ethers of fatty alcohols, condensation products of ethylene oxide-propylene oxide, alkyl polyethers, esters of sorbitanic fatty acid, esters of polyoxyethylenesorbitanic fatty acid, and sorbitanic esters of polyoxyethylene.

14. The method according to claim 13 wherein said emulsifiers are selected from: alkylarylpolyglycol ethers and calcium salts of alkylarylsulfonic acids.

15. The method according to claim 1 wherein the treating is performed with benzodioxole derivative of formula II:

(II)

at a concentration from 50 to 800 grams/hectare.

16. The method according to claim 15 wherein said concentration is from 100 to 400 grams/hectare.

17. The method according to claim 16 wherein the treating is repeated up to three times per vegetative cycle.

18. The method according to claim 17 wherein at least one treating is performed at the end of the vegetative cycle.

19. The method according to claim 15 wherein said treating is carried out by nebulisation.

20. The method according to claim 16 wherein said concentration is from 200 to 350 grams/hectare.

21. The method according to claim 19 wherein the treating is concentrated on the air-exposed areas of the plant.

* * * * *